United States Patent
Lee et al.

(10) Patent No.: US 9,567,613 B2
(45) Date of Patent: *Feb. 14, 2017

(54) RECOMBINANT MICROORGANISM HAVING ENHANCED BUTANOL PRODUCING ABILITY AND METHOD FOR PRODUCING BUTANOL USING THE SAME

(71) Applicant: GS CALTEX CORPORATION, Seoul (KR)

(72) Inventors: Sang-Hyun Lee, Daejeon (KR); Moon-Ho Eom, Daejeon (KR)

(73) Assignee: GS CALTEX CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/418,401

(22) PCT Filed: Mar. 11, 2013

(86) PCT No.: PCT/KR2013/001951
§ 371 (c)(1),
(2) Date: Jan. 29, 2015

(87) PCT Pub. No.: WO2014/021533
PCT Pub. Date: Feb. 6, 2014

(65) Prior Publication Data
US 2015/0299740 A1   Oct. 22, 2015

(30) Foreign Application Priority Data

Jul. 30, 2012   (KR) .................. 10-2012-0083547

(51) Int. Cl.
| | | |
|---|---|---|
| C12N 1/21 | (2006.01) | |
| C12P 7/16 | (2006.01) | |
| C12N 9/04 | (2006.01) | |
| C12N 9/10 | (2006.01) | |
| C12N 15/52 | (2006.01) | |
| C12N 9/02 | (2006.01) | |
| C12N 9/12 | (2006.01) | |

(52) U.S. Cl.
CPC .............. *C12P 7/16* (2013.01); *C12N 9/0006* (2013.01); *C12N 9/0008* (2013.01); *C12N 9/1029* (2013.01); *C12N 9/1217* (2013.01); *C12N 9/13* (2013.01); *C12N 15/52* (2013.01); *C12Y 101/01001* (2013.01); *C12Y 203/01008* (2013.01); *C12Y 207/02007* (2013.01); *C12Y 208/03008* (2013.01); *C12Y 102/01003* (2013.01); *Y02E 50/10* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 1,315,585 A | 9/1919 | Weizmann | |
| 8,765,446 B2 * | 7/2014 | Lee ..................... | C12N 9/0006 435/160 |
| 9,096,872 B2 * | 8/2015 | Lee ..................... | C12N 9/0006 |
| 2009/0047718 A1 | 2/2009 | Blaschek et al. | |
| 2011/0027845 A1 | 2/2011 | Lee et al. | |
| 2012/0301936 A1 * | 11/2012 | Lee ..................... | C12N 9/0006 435/160 |

FOREIGN PATENT DOCUMENTS

| | | | |
|---|---|---|---|
| KR | 1020080077080 A | 8/2008 | |
| KR | 1020090066951 A | 6/2009 | |
| KR | 1020110033087 A | 3/2011 | |
| KR | 1020110033089 A | 3/2011 | |
| KR | WO 2011037414 A2 * | 3/2011 | ........... C12N 9/0006 |
| WO | 2009082148 A2 | 7/2009 | |
| WO | 2011037415 A2 | 3/2011 | |
| WO | WO 2012045022 A2 * | 4/2012 | ........... C12N 9/0006 |

OTHER PUBLICATIONS

Yu et al., "Ctfab and adhE2 can induce acetone production and increase butanol production yield from glucose in clostridium tyrobutyricum", Conference Proceedings of American Institute of Chemical Engineers 2012 Annual Meeting, Dec. 2012, 2 pages.*
Jang et al., 2012. Enhanced butanol production obtained by reinforcing the direct butanol-forming route in Clostridium acetobutylicum. mBio 3(5):e00314-12, 9 pages.*
Kuit et al., Appl. Microbiol. Biotechnol. 94:729-741, Jan. 2012.*
Green et al., "Genetic manipulation of acid formation pathways by gene inactivation in Clostridium acetobutylicum ATCC 824", Microbiol. 142:2079-2086, 1996.*
Takashi Tsuchida et al., Direct Synthesis of n-Butanol from Ethanol over Nonstoichiometric Hydroxyapatite, 2006, pp. 8634-8642, vol. 45, Ind. Eng. Chem. Res.
Jin Young Lee et al., Metabolic engineering of Clostridium acetobutylicum M5 for highly selective butanol production, 2009, pp. 1432-1440, vol. 4, Biotechnol.
Yu Jiang et al., Disruption of the acetoacetate decarboxylase gene in solvent-producing clostridium acetobutylicum increases the butanol ratio, 2009, pp. 284-291, vol. 11, Metabolic Engineering.
T. C. Ezeji et al., Acetone butanol ethanol (ABE) production from concentrated substrate: reduction in substrate inhibition by fed-batch technique and prodcut inhibition by gas stripping, 2004, pp. 653-658, vol. 63, Appl Microbiol Biotechnol.
Peter Durre, Biobutanol: An attractive biofuel, 2007, pp. 1525-1534, vol. 2, Biotechnol.
International Search Report for PCT/KR2013/001951 mailed on Jun. 27, 2013.

* cited by examiner

*Primary Examiner* — David J Steadman
(74) *Attorney, Agent, or Firm* — Hauptman Ham, LLP

(57) ABSTRACT

The present invention relates to a microorganism having an acetyl CoA biosynthesis pathway and a butyryl CoA biosynthesis pathway; the microorganism being a recombinant microorganism having an increased ability to produce butanol, wherein a pathway for converting acetyl CoA into acetate is suppressed, and a pathway for converting acetate into acetyl CoA and a pathway for converting butyryl CoA into butanol are promoted. Also, the present invention concerns a method for producing butanol by using the recombinant microorganism.

10 Claims, 9 Drawing Sheets

Fig. 8 atgaaagtcacaacagtaaaggaattagatgaaaaactcaaggtaattaaagaagctcaaaaaaaattctcttgttactcgcaagaaatggttgat
gaaatctttagaaatgcagcaatggcagcaatcgacgcaaggatagagctagcaaaagcagctgttttggaaaccggtatgggcttagttgaa
gacaaggttataaaaaatcattttgcaggcgaatacatctataacaaatataaggatgaaaaaacctgcggtataattgaacgaaatgaaccctac
ggaattacaaaaatagcagaacctataggagttgtagctgctataatccctgtaacaaaccccacatcaacaacaatatttaaatccttaatatccctt
aaaactagaaatggaattttcttttcgcctcacccaagggcaaaaaaatccacaatactagcagctaaaacaatacttgatgcagccgttaagagt
ggtgccccggaaaatataataggttggatagatgaaccttcaattgaactaactcaatatttaatgcaaaaagcagatataaccttgcaactggtg
gtccctcactagttaaatctgcttattcttccggaaaaccagcaataggtgttggtccgggtaacaccccagtaataattgatgaatctgctcatataa
aaatggcagtaagttcaattatattatccaaaacctatgataatggtgttatatgtgcttctgaacaatctgtaatagtcttaaaatccatatataacaa
ggtaaaagatgagttccaagaaagaggagcttatataataaagaaaaacgaattggataaagtccgtgaagtgattttaaagatggatccgtaa
accctaaaatagtcggacagtcagcttatactatagcagctatggctggcataaaagtacctaaaaccacaagaatattaataggagaagttacct
ccttaggtgaagaagaaccttttgcccacgaaaaactatctcctgttttggctatgtatgaggctgacaattttgatgatgcttaaaaaaagcagta
actctaataaacttaggaggcctcggccatacctcaggaatatatgcagatgaaatataaaagcacgagataaaatagatagatttagtagtgccat
gaaaaccgtaagaacctttgtaaatatcccaacctcacaaggtgcaagtggagatctatataattttagaataccaccttctttcacgcttggctgcg
gattttggggaggaaattctgtttccgagaatgttggtccaaaacatcttttgaatattaaaaccgtagctgaaaggagagaaaacatgctttggtt
tagagttccacataaagtatattttaagttcggttgtcttcaatttgctttaaaagatttaaaagatctaaagaaaaaaagagcctttatagttactgat
agtgacccctataatttaaactatgttgattcaataataaaaatacttgagcacctagatattgattttaaagtatttaataaggttggaagagaagct
gatcttaaaaccataaaaaaagcaactgaagaaatgtcctcctttatgccagacactataatagcttaggtggtaccccctgaaatgagctctgcaa
agctaatgtgggtactatatgaacatccagaagtaaaatttgaagatcttgcaataaaatttatggacataagaaagagaatatatactttcccaaa
actcggtaaaaaggctatgttagttgcaattacaacttctgctggttccggttctgaggttactccttttgcttttagtaactgacaataacactggaaat
aagtacatgttagcagattatgaaatgacaccaaatatggcaattgtagatcagaacttatgatgaaaatgccaaagggattaaccgcttattca
ggtatagatgcactagtaaatagtatagaagcatacacatccgtatatgcttcagaatacacaaacggactagcactagaggcaatacgattaata
tttaaatatttgcctgaggcttacaaaaacggaagaaccaatgaaaaagcaagagagaaaatggctcacgcttcaactatggcaggtatggcatc
cgctaatgcatttctaggtctatgtcattccatggcaataaaattaagttcagaacacaatattcctagtggcattgccaatgcattactaatagaaga
agtaataaaatttaacgcagttgataatcctgtaaaacaagcccttgcccacaatataagtatccaaacaccatatttagatatgctcgaattgcag
attatataaagcttggaggaaatactgatgaggaaaaggtagatctcttaattaacaaaatacatgaactaaaaaaagctttaaatataccaacttc
aataaaggatgcaggtgttttggaggaaaacttctattcctcccttgatagaatatctgaacttgcactagatgatcaatgcacaggcgctaatccta
gatttcctcttacaagtgagataaaagaaatgtatataaattgtttttaaaaaacaaccttaa

Fig. 9 atgaactctaaaataattagatttgaaaatttaaggtcattctttaaagatgggatgacaattatgattggaggttttttaaactgtggcactccaacc
aaattaattgatttttagttaatttaaatataaagaatttaacgattataagtaatgatacatgttatcctaatacaggtattggtaagttaatatcaaat
aatcaagtaaaaaagcttattgcttcatatataggcagcaacccagatactggcaaaaaacttttaataatgaacttgaagtagagctctctcccca
aggaactctagtggaaagaatacgtgcaggcggatctggcttaggtggtgtactaactaaaacaggtttaggaactttgattgaaaaaggaaag
aaaaaaatatctataaatggaacggaatatttgttagagctacctcttacagccgatgtagcattaattaaaggtagtattgtagatgaggccggaa
acaccttctataaaggtactactaaaaactttaatccctatatggcaatggcagctaaaaccgtaatagttgaagctgaaaatttagttagctgtgaa
aaactagaaaaggaaaaagcaatgaccccccggagttcttataaattatatagtaaaggagcctgcataaaatgattaatgataaaaaacctagcga
aagaaataatagccaaaagagttgcaagagaattaaaaaaatggtcaacttgtaaacttaggtgtaggtcttcctaccatggttgcagattatatacc
aaaaaatttcaaaattacttccaatcagaaaacggaatagttggaatgggcgctagtcctaaaataaatgaggcagataaagatgtagtaaatgc
aggaggagactatacaacagtacttcctgacggcacattttcgatagctcagtttcgttttcactaatccgtggtggtcacgtagatgttactgttta
ggggctctccaggtagatgaaaagggtaatatagccaattggattgttcctggaaaaatgctctctggtatgggtggagctatggatttagtaaat
ggagctaagaaagtaataattgcaatgagacatacaaataaaggtcaacctaaaattttaaaaaaatgtacacttcccctcacggcaaagtctcaa
gcaaatctaattgtaacagaacttggagtaattgaggttattaatgatggtttacttctcactgaaattaataaaaacacaaccattgatgaaataag
gtctttaactgctgcagatttactcatatccaatgaacttagacccatggctgtttag

```
                        SEQUENCE LISTING

<160> NUMBER OF SEQ ID NOS: 8

<210> SEQ ID NO 1
<211> LENGTH: 2589
<212> TYPE: DNA
<213> ORGANISM: Clostridium acetobutylicum

<400> SEQUENCE: 1
atgaaagtca caacagtaaa ggaattagat gaaaaactca aggtaattaa agaagctcaa      60
aaaaaattct cttgttactc gcaagaaatg gttgatgaaa tctttagaaa tgcagcaatg     120
gcagcaatcg acgcaaggat agagctagca aaagcagctg ttttggaaac cggtatgggc     180
ttagttgaag acaaggttat aaaaaatcat tttgcaggcg aatacatcta taacaaatat    240
aaggatgaaa aaacctgcgg tataattgaa cgaaatgaac cctacggaat tacaaaaata     300
gcagaaccta taggagttgt agctgctata atccctgtaa caaacccccac atcaacaaca    360 atatttaaat ccttaatatc ccttaaaact agaaatggaa ttttcttttc gcctcaccca     420
agggcaaaaa atccacaat actagcagct aaaacaatac ttgatgcagc cgttaagagt      480
ggtgccccgg aaaatataat aggttggata gatgaaccctt caattgaact aactcaatat    540
ttaatgcaaa aagcagatat aaccccttgca actggtggtc cctcactagt taaatctgct    600
tattcttccg gaaaaccagc aataggtgtt ggtccgggta cacccccagt aataattgat    660
gaatctgctc atataaaaat ggcagtaagt tcaattatat tatccaaaac ctatgataat    720
ggtgttatat gtgcttctga acaatctgta atagtcttaa aatccatata taacaaggta    780
aaagatgagt tccaagaaag aggagcttat ataataaaga aaacgaatt ggataaagtc     840 cgtgaagtga tttttaaaga tggatccgta aaccctaaaa tagtcggaca gtcagcttat    900
actatagcag ctatggctgg cataaaagta cctaaaacca caagaatatt aataggagaa    960
gttacctcct taggtgaaga agaacctttt gcccacgaaa aactatctcc tgttttggct   1020
atgtatgagg ctgacaattt tgatgatgct ttaaaaaaag cagtaactct aataaactta   1080
ggaggcctcg gccatacctc aggaatatat gcagatgaaa taaaagcacg agataaaata   1140
gatagattta gtagtgccat gaaaaccgta agaaccttttg taaatatccc aacctcacaa   1200
ggtgcaagtg gagatctata taatttttaga ataccacctt ctttcacgct tggctgcgga   1260
ttttggggag gaaattctgt ttccgagaat gttggtccaa aacatctttt gaatattaaa   1320
accgtagctg aaaggagaga aaacatgctt tggtttagag ttccacataa agtatatttt   1380
aagttcggtt gtcttcaatt tgctttaaaa gatttaaaag atctaaagaa aaaaagagcc   1440
```

```
tttatagtta ctgatagtga ccc ctataat ttaaactatg ttgattcaat aataaaaata    1500
cttgagcacc tagatattga ttttaaagta tttaataagg ttggaagaga agctgatctt    1560
aaaaccataa aaaaagcaac tgaagaaatg tcctccttta tgccagacac tataatagct    1620
ttaggtggta cccctgaaat gagctctgca aagctaatgt gggtactata tgaacatcca    1680
gaagtaaaat ttgaagatct tgcaataaaa tttatggaca taagaaagag aatatatact    1740
ttcccaaaac tcgtaaaaaa ggctatgtta gttgcaatta caacttctgc tggttccggt    1800
tctgaggtta ctccttttgc tttagtaact gacaataaca ctggaaataa gtacatgtta    1860
gcagattatg aaatgacacc aaatatggca attgtagatg cagaacttat gatgaaaatg    1920
ccaaagggat taaccgctta ttcaggtata gatgcactag taaatagtat agaagcatac    1980
acatccgtat atgcttcaga atacacaaac ggactagcac tagaggcaat acgattaata    2040
tttaaatatt tgcctgaggc ttacaaaaac ggaagaacca atgaaaaagc aagagagaaa    2100
atggctcacg cttcaactat ggcaggtatg gcatccgcta atgcatttct aggtctatgt    2160
cattccatgg caataaaatt aagttcagaa cacaatattc ctagtggcat tgccaatgca    2220
ttactaatag aagaagtaat aaaatttaac gcagttgata atcctgtaaa acaagcccct    2280
tgcccacaat ataagtatcc aaacaccata tttagatatg ctcgaattgc agattatata    2340
aagcttggag gaaatactga tgaggaaaag gtagatctct taattaacaa aatacatgaa    2400
ctaaaaaaag ctttaaatat accaacttca ataaggatg caggtgtttt ggaggaaaac    2460
ttctattcct cccttgatag aatatctgaa cttgcactag atgatcaatg cacaggcgct    2520
aatcctagat ttcctcttac aagtgagata aagaaatgt atataaattg ttttaaaaaa    2580
caaccttaa                                                           2589

<210> SEQ ID NO 2
<211> LENGTH: 1324
<212> TYPE: DNA
<213> ORGANISM: Clostridium acetobutylicum

<400> SEQUENCE: 2
atgaactcta aaataattag atttgaaaat ttaaggtcat tctttaaaga tgggatgaca     60
attatgattg gaggtttttt aaactgtggc actccaacca aattaattga ttttttagtt    120
aatttaaata taaagaattt aacgattata agtaatgata catgttatcc taatacaggt    180
attggtaagt taatatcaaa taatcaagta aaaaagctta ttgcttcata taggcagc     240 aacccagata ctggcaaaaa acttttttaat aatgaacttg aagtagagct ctctccccaa    300
ggaactctag tggaaagaat acgtgcaggc ggatctggct taggtggtgt actaactaaa    360
acaggtttag gaactttgat tgaaaaagga agaaaaaaa tatctataaa tggaacggaa    420
tatttgttag agctacctct tacagccgat gtagcattaa ttaaaggtag tattgtagat    480
gaggccggaa acaccttcta taaggtact actaaaaact ttaatcccta tatggcaatg    540
gcagctaaaa ccgtaatagt tgaagctgaa aatttagtta gctgtgaaaa actagaaaag    600
gaaaaagcaa tgacccccgg agttcttata aattatatag taaaggagcc tgcataaaat    660
gattaatgat aaaaacctag cgaaagaaat aatagccaaa agagttgcaa gagaattaaa    720
aaatggtcaa cttgtaaact aggtgtagg tcttcctacc atggttgcag attatatacc    780
aaaaaatttc aaaattactt tccaatcaga aacggaata gttggaatgg gcgctagtcc    840
taaaataaat gaggcagata agatgtgagt aaatgcagga ggagactata caacagtact    900
tcctgacggc acatttttcg atagctcagt ttcgttttca ctaatccgtg gtggtcacgt    960
```

```
agatgttact gttttagggg ctctccaggt agatgaaaag ggtaatatag ccaattggat    1020
tgttcctgga aaaatgctct ctggtatggg tggagctatg gatttagtaa atggagctaa    1080
gaaagtaata attgcaatga gacatacaaa taaaggtcaa cctaaaattt taaaaaaatg    1140
tacacttccc ctcacggcaa agtctcaagc aaatctaatt gtaacagaac ttggagtaat    1200
tgaggttatt aatgatggtt tacttctcac tgaaattaat aaaaacacaa ccattgatga    1260
aataaggtct ttaactgctg cagatttact catatccaat gaacttagac ccatggctgt    1320
ttag                                                                1324

<210> SEQ ID NO 3
<211> LENGTH: 39
<212> TYPE: DNA
<213> ORGANISM: Artificial Sequence
<220> FEATURE:
<223> OTHER INFORMATION: primer: AdhE1-UP-PstI

<400> SEQUENCE: 3
cacctgcaga tgaaagtcac aacagtaaag gaattagat                           39

<210> SEQ ID NO 4
<211> LENGTH: 41
<212> TYPE: DNA
<213> ORGANISM: Artificial Sequence
<220> FEATURE:
<223> OTHER INFORMATION: primer: AdhE1-DN-XhoI

<400> SEQUENCE: 4
cacctcgagt taaggttgtt ttttaaaaca atttatatac a                        41

<210> SEQ ID NO 5
<211> LENGTH: 44
<212> TYPE: DNA
<213> ORGANISM: Artificial Sequence
<220> FEATURE:
<223> OTHER INFORMATION: primer: CtfAB-UP-BglII

<400> SEQUENCE: 5
cacagatcta tgaactctaa ataattaga tttgaaaatt taag                      44

<210> SEQ ID NO 6
<211> LENGTH: 44
<212> TYPE: DNA
<213> ORGANISM: Artificial Sequence
<220> FEATURE:
<223> OTHER INFORMATION: primer: CtfAB-DN-EcoRI

<400> SEQUENCE: 6
cacgaattct aaacagcca tgggtctaag ttcattggat atga                      44

<210> SEQ ID NO 7
<211> LENGTH: 35
<212> TYPE: DNA
<213> ORGANISM: Artificial Sequence
<220> FEATURE:
<223> OTHER INFORMATION: primer: CtfAB-UP-XhoI

<400> SEQUENCE: 7
cacctcgaga cctttcatatt tcaactactt tttat                              35

<210> SEQ ID NO 8
<211> LENGTH: 36
<212> TYPE: DNA
```

```
<213> ORGANISM: Artificial Sequence
<220> FEATURE:
<223> OTHER INFORMATION: primer: E1AB-DN-SalI

<400> SEQUENCE: 8
tacgcgtcga cgccagtaaa agagattgtt tctagc                                36
```

RECOMBINANT MICROORGANISM HAVING ENHANCED BUTANOL PRODUCING ABILITY AND METHOD FOR PRODUCING BUTANOL USING THE SAME

CROSS REFERENCE TO RELATED APPLICATION

This application claims the priority of Korean Patent Application No. 10-2012-0083547 filed on Jul. 30, 2012 in the Korean Patent and Trademark Office. Further, this application is the National Phase application of International Application No. PCT/KR2013/001951 filed on Mar. 11, 2013, which is incorporated herein by reference in its entirety.

TECHNICAL FIELD

The present invention relates to a recombinant microorganism having enhanced butanol producing ability and a method for producing butanol using the same.

BACKGROUND ART

Butanol is an intermediate compound with a very wide range of uses, such as in cosmetics, perfumes, hormones, hygiene products, industrial coating agents, paint additives, fibers, plastic monomers, medical supplies, vitamins, antibiotics, agricultural chemicals, and the like, and is very useful (Dune, Biotechnol J, 2:1525-1534, 2007).

Up to the 1980s, methods for producing butanol, acetone and ethanol by fermenting sugars with *Clostridium* strains were utilized as typical methods for preparing butanol (Weizmann, U.S. Pat. No. 1,315,585). Since the 1980s, an oxo process for synthesizing butanol from propylene originated from petroleum has been widely used. However, the method for preparing butanol based on petroleum has drawbacks in that the process is complicated due to the use of high temperature and high pressure, and a large amount of hazardous waste and carbon dioxide are released therefrom (Tsuchida et al., Ind. Eng. Chem. Res., 45:8634, 2006). Recently, the demand for eco-friendly production of butanol from renewable sources through microbial fermentation has greatly increased.

However, in order to produce butanol at industrially applicable levels using microorganisms, it is essential that the production method should have good butanol selectivity, yield and productivity, namely butanol production amount per unit hour. However, among wild type and recombinant microorganisms for producing bio-butanol, a microorganism satisfying all these conditions has yet to be found.

Specifically, a wild type *Clostridium acetobutylicum* Strain ATCC824 is known to produce acetone, ethanol and butanol in a mass ratio of about 3:1:6 through fermentation and a small amount of acetic acid and butyric acid, wherein the yield of the wild type strain is about 25%, and the final concentration is about 10 g/L or so. Like *Clostridium acetobutylicum*, microorganisms having an acetyl-CoA biosynthetic pathway and a butyryl-CoA biosynthetic pathway are generally known to synthesize acetone, butanol and ethanol in the pathways as shown in FIG. 1. Recently, with the development of metabolic engineering, endeavors to produce butanol more effectively have continued. Especially, since the genomic sequence of *Clostridium acetobutylicum* is recently disclosed, research relating to metabolic pathway manipulation has been actively performed.

For example, co-overexpression of adhE1 and ctfAB genes in *Clostridium acetobutylicum* M5 in which a megaplasmid having butanol production related genes (adc, ctfAB and adhE1 (alcohol/aldehyde dehydrogenase) and adhE2 (alcohol/aldehyde dehydrogenase)) was deleted showed that butanol selectivity was enhanced to a mass ratio of 0.78, but the co-overexpression had limits in that productivity and yield were greatly reduced as growth of the strain was inhibited and the production of acetic acid increased (Lee, et al., Biotechnology Journal, 4:1432-1440, 2009; Lee, et al., WO 2009/082148).

In the case where pta converting acetyl-CoA into acetate is deleted, and in the case where both pta and buk converting butyryl-CoA into butyrate are deleted and aad (alcohol/aldehyde dehydrogenase) is overexpressed, both cases are reported to enhance butanol concentration, selectivity and yield. However, both cases still have limits in view of productivity and stability of strains (Lee et al., WO 2011/037415). Furthermore, in the case where CtfB coding CoA transferase (CoAT) was further deleted from a mutant strain from which pta and buk are deleted, the strain still shows low productivity (LEE et al., WO 2011/037415).

In addition, in the case where a mutant *Clostridium beijerinckii* BA101 strain derived by random mutation is subjected to fermentation utilizing maltodextrin as a carbon source, it is reported that 18.6 g/l, of butanol is produced (Ezeji et al., Appl. Microbiol. Biotechnol., 63:653, 2004). However, even if the recombinant strain is employed, the strain has no industrial applicability due to low production of final product, i.e. butanol.

In addition, reports say that the concentration of acetone is decreased and butanol selectivity is increased by deleting ctfAB encoding CoA transferase or adc (acetoacetate decarboxylase). However, this report has problems in view of strain stability and the final concentration of butanol less than 10 g/L (Jiang et al., Metab. Eng., 11(4-5):284-291, 2009).

The present inventors made research to find microorganisms having good butanol selectivity, yield and productivity. As a result, the present inventors found that a recombinant mutant microorganism capable of producing butanol with high yield, high selectivity and high productivity can be manufactured by deleting pta and buk simultaneously which are butyrate and acetate production related genes, and co-overexpressing CtfAB which encodes CoA transferase (CoAT) and adhE (alcohol/aldehyde dehydrogenase) which converts butyryl-CoA to butanol. Based on this finding, the present invention has been completed.

DISCLOSURE

Technical Problem

It is an object of the present invention to provide a recombinant microorganism having enhanced butanol producing ability.

Technical Solution

In order to achieve the object of the invention, the present invention provides a recombinant microorganism having enhanced butanol producing ability, wherein a pathway of converting acetyl-CoA to acetate is suppressed and a pathway of converting acetate to acetyl-CoA and a pathway of converting butyryl-CoA to butanol are promoted, in the microorganism having an acetyl-CoA biosynthetic pathway and a butyryl-CoA biosynthetic pathway.

In addition, the present invention provides a method for producing butanol including: culturing a recombinant microorganism according to the present invention; and harvesting butanol from the culture broth.

Advantageous Effects

The recombinant microorganism according to the present invention demonstrates excellent properties in terms of high butanol productivity, yield and butanol selectivity.

DESCRIPTION OF DRAWINGS

FIG. 8 shows a SEQ ID NO: 1.

FIG. 9 shows a SEQ ID NO: 2.

BEST MODE

The present invention relates to a recombinant microorganism having enhanced butanol producing ability, wherein a pathway of converting acetyl-CoA to acetate is suppressed and a pathway of converting acetate to acetyl-CoA and a pathway of converting butyryl-CoA to butanol are promoted, in the microorganism having an acetyl-CoA biosynthetic pathway and a butyryl-CoA biosynthetic pathway.

Further, the present invention relates to a method for producing butanol including: culturing the recombinant microorganism according to the present invention; and harvesting butanol from the culture broth.

Hereinafter, the present invention will be described in detail.

Recombinant Microorganism Having Enhanced Butanol Producing Ability

The recombinant microorganism according to the present invention is a recombinant microorganism having enhanced butanol producing ability, wherein a pathway of converting acetyl-CoA to acetate is suppressed and a pathway of converting acetate to acetyl-CoA and a pathway of converting butyryl-CoA to butanol are promoted, in the microorganism having an acetyl-CoA biosynthetic pathway and a butyryl-CoA biosynthetic pathway.

In addition, the recombinant microorganism according to the present invention is a recombinant microorganism having enhanced butanol producing ability, wherein a pathway of converting acetyl-CoA to acetate and a pathway of converting butyryl-CoA to butyrate are suppressed and a pathway of converting acetate to acetyl-CoA and a pathway of converting butyryl-CoA to butanol are promoted, in the microorganism having an acetyl-CoA biosynthetic pathway and a butyryl-CoA biosynthetic pathway.

Figure 1:
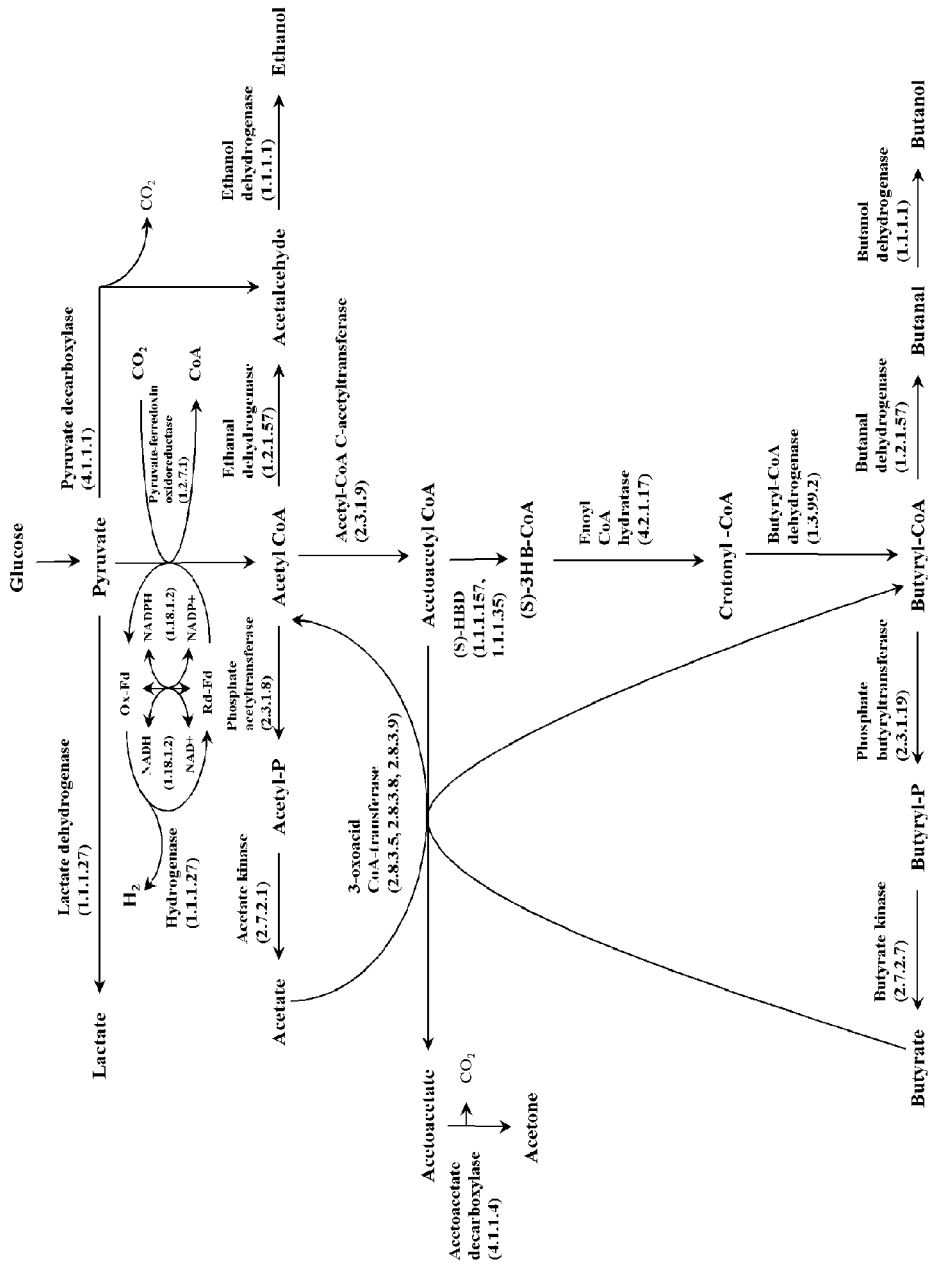
FIG. 1 shows synthetic pathways of acetone, butanol and ethanol in a microorganism having an acetyl-CoA biosynthetic pathway and a butyryl-CoA biosynthetic pathway.
Figure 2:
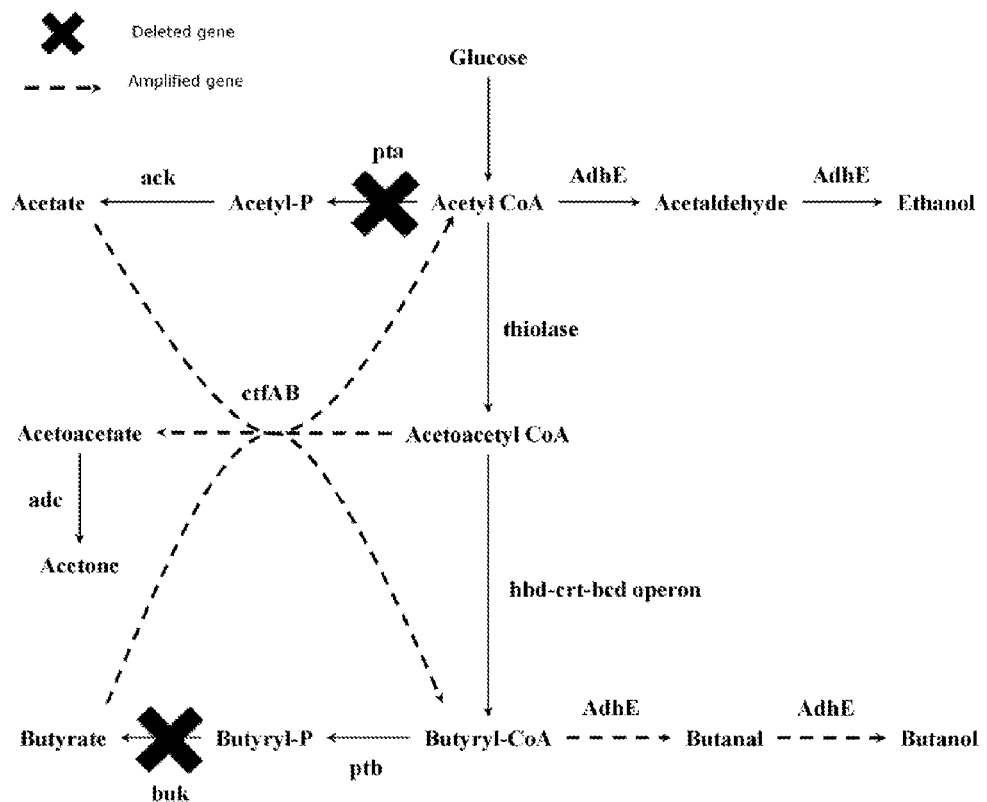
FIG. 2 shows one embodiment of the recombinant microorganism according to the present invention.

Further, as illustrated in FIG. 2, the recombinant microorganism according to the present invention is a recombinant microorganism having enhanced butanol producing ability, wherein a pathway of converting acetyl-CoA to acetate and a pathway of converting butyryl-CoA to butyrate are suppressed and a pathway of converting butyrate to butyryl CoA, a pathway of converting acetate to acetyl-CoA and a pathway of converting butyryl-CoA to butanol are promoted, in the microorganism having an acetyl-CoA biosynthetic pathway and a butyryl-CoA biosynthetic pathway.

Furthermore, the recombinant microorganism according to the present invention is a recombinant microorganism in which a gene encoding acetoacetate decarboxylase, namely, adc is not deleted.

Acetyl-CoA Biosynthetic Pathway

The acetyl-CoA biosynthetic pathway according to the present invention refers to a pathway of synthesizing acetyl-CoA from specific metabolites in microorganisms. The acetyl-CoA biosynthetic pathway according to the present invention may be a pathway of synthesizing acetyl-CoA from pyruvate or a pathway of synthesizing acetyl-CoA from acetate, and the like. The pathway of synthesizing acetyl-CoA from acetate may be regulated by CoA transferase.

Butyryl-CoA Biosynthetic Pathway

The butyryl-CoA biosynthetic pathway according to the present invention refers to a pathway of synthesizing butyryl-CoA from specific metabolites in microorganisms. The butyryl-CoA biosynthetic pathway may be a pathway of synthesizing butyryl-CoA from acetyl-CoA, a pathway of synthesizing butyryl-CoA from acetoacetyl-CoA, or a pathway of synthesizing butyryl-CoA from butyrate, and the like. The pathway of synthesizing butyryl-CoA from butyrate may be regulated by CoA transferase.

Microorganism Having Acetyl-CoA Biosynthetic Pathway and Butyryl-CoA Biosynthetic Pathway According to the present invention, the microorganism having an acetyl-CoA biosynthetic pathway and a butyryl-CoA biosynthetic pathway may be any microorganisms having the aforementioned biosynthetic pathways and is not specifically limited. Further, the microorganism according to the present invention may be a microorganism having a wild type of acetyl-CoA biosynthetic pathway and a wild type of butyryl-CoA biosynthetic pathway or a recombinant microorganism having those pathways through genetic recombination. Preferably, the microorganism is *Clostridium*, without being limited thereto.

Suppression of Pathway of Converting Acetyl-CoA to Acetate

The biosynthesized acetyl-CoA may be converted to acetate via acetyl phosphate. This pathway may be suppressed by inhibiting the step of converting acetyl-CoA to acetyl phosphate or the step of converting acetyl phosphate to acetate. These steps may be inhibited by any known method such as expression regulation of enzymes regulating each step or inhibition of enzyme activity.

For example, phosphotransacetylase regulates conversion of acetyl-CoA to acetyl phosphate Inhibition of phosphotransacetylase may suppress the pathway of converting acetyl-CoA to acetate Inhibition of phosphotransacetylase may be performed through suppressing the expression of phosphotransacetylase, inhibiting the enzyme activity of phosphotransacetylase, and the like. For example, phosphotransacetylase may be suppressed by those skilled in the art through selection of a suitable method, such as deletion of a gene encoding phosphotransacetylase, namely, pta; mutations in the gene (mutation such that normal gene expression is inhibited by variation, substitution or deletion of a partial base sequence, insertion of a partial base sequence, or the like); or regulation of gene expression during transcription or translation, and the like.

In addition, acetate kinase (ack) regulates conversion of acetyl phosphate to acetate Inhibition of acetate kinase may suppress the pathway of converting acetyl-CoA to acetate Inhibition of acetate kinase may be performed by suppressing the expression of acetate kinase, inhibiting the enzyme activity of acetate kinase, and the like. For example, acetate kinase may be suppressed by those skilled in the art through selection of a suitable method, such as deletion of a gene encoding acetate kinase, namely, ack; mutations in the gene (mutation such that normal gene expression is inhibited by variation, substitution or deletion of a partial base sequence, insertion of a partial base sequence, or the like); or regulation of gene expression during transcription or translation, and the like.

Suppression of Pathway of Converting Butyryl-CoA to Butyrate

The biosynthesized butyryl-CoA may be converted to butyrate via butyryl phosphate. This pathway may be suppressed by inhibiting the step of converting butyryl-CoA to butyryl phosphate or the step of converting butyryl phosphate to butyrate. These steps may be inhibited by a known method such as expression regulation of enzymes regulating each step or inhibition of enzyme activity.

For example, butyrate kinase regulates conversion of butyryl phosphate to butyrate Inhibition of butyrate kinase may suppress the pathway of converting acetyl-CoA to butyrate Inhibition of butyrate kinase may be performed through suppressing the expression of butyrate kinase, inhibiting the enzyme activity of butyrate kinase, and the like. For example, butyrate kinase may be inhibited by those skilled in the art by selecting a suitable method, such as deletion of a gene encoding butyrate kinase, namely, buk; mutations in the gene (mutation such that normal gene expression is inhibited by variation, substitution or deletion of a partial base sequence, insertion of a partial base sequence, or the like); or regulation of gene expression during transcription or translation, and the like.

Further, phosphotransbutylase regulates conversion of butyryl CoA to butyryl phosphate Inhibition of phosphotransbutylase may suppress the pathway of converting butyryl-CoA to butyrate Inhibition of phosphotransbutylase may be performed by suppressing the expression phosphotransbutylase, enzyme activity inhibition of phosphotransbutylase, and the like. For example, phosphotransbutylase may be inhibited by those skilled in the art through selection of a suitable method, such as deletion of a gene encoding phosphotransbutylase, namely, ptb; mutations in the gene (mutation such that normal gene expression is inhibited by variation, substitution or deletion of a partial base sequence, insertion of a partial base sequence, or the like); or regulation of gene expression during transcription or translation, and the like.

Promotion of Pathway of Converting Butyrate to Butyryl-CoA

CoA transferase regulates conversion of butyrate to butyryl-CoA. The pathway of converting butyrate to butyryl-CoA may be promoted by increasing activity of CoA transferase. Increase of CoA transferase activity may be performed by increasing expression of CoA transferase, enzyme activity of CoA transferase, and the like. For example, the CoA transferase activity may be increased by those skilled in the art through selection of a suitable method, such as introduction, amplification, and rearrangement of a gene encoding CoA transferase, namely, cftA or ctfB (hereinafter, "ctfAB"), regulation of gene expression during transcription or translation, and the like.

Promotion of Pathway of Converting Acetate to Acetyl-CoA

CoA transferase regulates conversion of acetate to acetyl-CoA. The pathway of converting acetate to acetyl-CoA may be promoted by increasing activity of CoA transferase. Increase of CoA transferase activity may be performed by increasing expression of CoA transferase, enzyme activity of CoA transferase, and the like. For example, the CoA transferase activity may be increased by those skilled in the art through selection of a suitable method, such as introduction, amplification, and rearrangement of a gene encoding CoA transferase, namely, ctfAB, regulation of gene expressions during transcription or translation, and the like.

Promotion of Pathway of Converting Butyryl-CoA to Butanol

The biosynthesized butyryl-CoA may be converted to butanol via butanal. This pathway may be promoted by accelerating the step of converting butyryl-CoA to butanal or the step of converting butanal to butanol. Each step may be promoted by a known method such as increase of enzyme activity.

For example, aldehyde/alcohol dehydrogenase regulates conversion of butyryl-CoA to butanal and conversion of butanal to butanol. The pathway of converting butyryl-CoA to butanol may be promoted by increasing activity of aldehyde/alcohol dehydrogenase. Increase of aldehyde/alcohol dehydrogenase activity may be performed by increasing expression of aldehyde/alcohol dehydrogenase, enzyme activity of aldehyde/alcohol dehydrogenase, and the like. For example, the aldehyde/alcohol dehydrogenase activity may be increased by those skilled in the art through selection of a suitable method, such as introduction, amplification, and rearrangement of a gene encoding aldehyde/alcohol dehydrogenase, namely, adhE, regulation of gene expressions during transcription or translation, and the like.

Acetoacetate Decarboxylase

Acetoacetate decarboxylase regulates conversion of acetoacetate to acetone. Therefore, it is possible to enhance the production of butanol through deletion of a gene encoding acetoacetate decarboxylase, namely, adc, thereby inhibiting the production of acetone (WO 2009/082148). However, the recombinant microorganism according to the present invention has a problem of significant reduction in butanol productivity and yield when adc is further deleted. It is determined that this is because acetoacetate is not capable of being converted to acetone, thereby causing cytotoxicity. Consequently, in the recombinant microorganism according to the present invention, a gene encoding acetoacetate, namely, adc, is not deleted.

Enhancement of Butanol Producing Ability

Enhancement of butanol producing ability refers to the production of butanol with high selectivity (the ratio of butanol among produced ABE (Acetone, Butanol, Ethanol)), productivity (the amount of butanol produced per unit hour) and yield (the amount of ABE produced as compared to the amount of carbon sources consumed in the production). Preferably, enhancement of butanol producing ability means that the production of butanol is performed such that butanol selectivity is 60% or more, butanol productivity is 1.3 g/L/h or more, and yield is 28% or more based on a batch culture method.

Method for Producing Butanol

The method for producing butanol according to the present invention includes culturing a recombinant microorganism according to the present invention; and harvesting butanol from the culture broth.

The culture method refers to any culture method generally used to produce alcohols using microorganisms, without being particularly limited. For example, the culture method according to the present invention may include liquid culture, solid culture, batch culture, continuous culture, and fed-batch culture, without being particularly limited. The present invention may be realized by those skilled in the art through selection of a suitable culture method.

The method for harvesting butanol refers to any method generally used to collect bio-alcohols, without being particularly limited. For example, the method for harvesting butanol according to the present invention may be performed using separation membranes, distillation, or the like. Further, microorganism culture and butanol harvesting may be performed simultaneously or sequentially. For example, the microorganism may be continuously cultured while collecting butanol.

MODE FOR INVENTION

The advantages and features of the present invention, and methods for accomplishing the same will be described in more detail with reference to the following examples together with the accompanying drawings. It should be understood that the present invention may be embodied in different ways, and that the embodiments are given to provide complete disclosure of the invention and to provide thorough understanding of the invention to a person having ordinary knowledge in the art to which the present invention pertains. The present invention is only defined by the appended claims and equivalents thereof.

Materials and Methods

With any known method as disclosed in WO2011/037415, *Clostridium acetobutylicum* ATCC824 Δpta, *Clostridium acetobutylicum* ATCC824 Δbuk, *Clostridium acetobutylicum* ATCC824 Δpta Δbuk and *Clostridium acetobutylicum* ATCC824 Δpta Δbuk Δadc were constructed.

In evaluation of bio-butanol production ability of recombinant *C. acetobutylicum* strains, butanol selectivity (the ratio of butanol among produced mixed solvent (ABE: Acetone, Butanol, Ethanol), butanol productivity and yield were calculated as follows:

Butanol selectivity (%): The amount of produced butanol (g)/the amount of produced ABE (g)×100

Butanol productivity (g/L/h): The amount of produced butanol per unit hour, unit volume (wherein, butanol productivity is calculated based on exponential phase)

Yield (%): The amount of produced ABE (g)/Carbon source (g)×100

ABE productivity (g/L/h): The amount of ABE produced per unit hour, unit volume

Experimental Example 1

Construction of Plasmid

Construction of pGS1-pTh1AdhE1 and pGS1-pTh1CtfAB

*Clostridium acetobutylicum* strain ATCC824 was streaked on RCM solid media, followed by culturing anaerobically for 48 hours. A single colony from the streaked solid medium was cultured in 3 ml of RCM liquid media for 18 hours, followed by centrifugation of the culture broth, thereby harvesting cells. After washing the harvested cells with 10 ml of Tris buffer, the chromosome of the strain was isolated using Wizard Genomic DNA purification Kit (Promega, USA).

The isolated chromosome was used as a template for amplifying AdhE1 (SEQ ID NO: 1) using AdhE1-UP-PstI (SEQ ID NO: 3) and AdhE1-DN-XhoI (SEQ ID NO: 4) primers. 100 μl of PCR reaction mixture was prepared by adding 250 μM of dNTP, 20 pmol of each primer, 1.5 mM MgCl$_2$, 10 μl of 10× buffer, 100 ng of DNA template, and 5 units of pfu polymerase. The reaction mixture was subjected to initial denaturation at 95° C. for 5 minutes, denatured at 95° C. for one minute, annealed at 50° C. for one minute, and then polymerized at 72° C. for 2 minutes. These steps were repeated 25 times.

Figure 3:
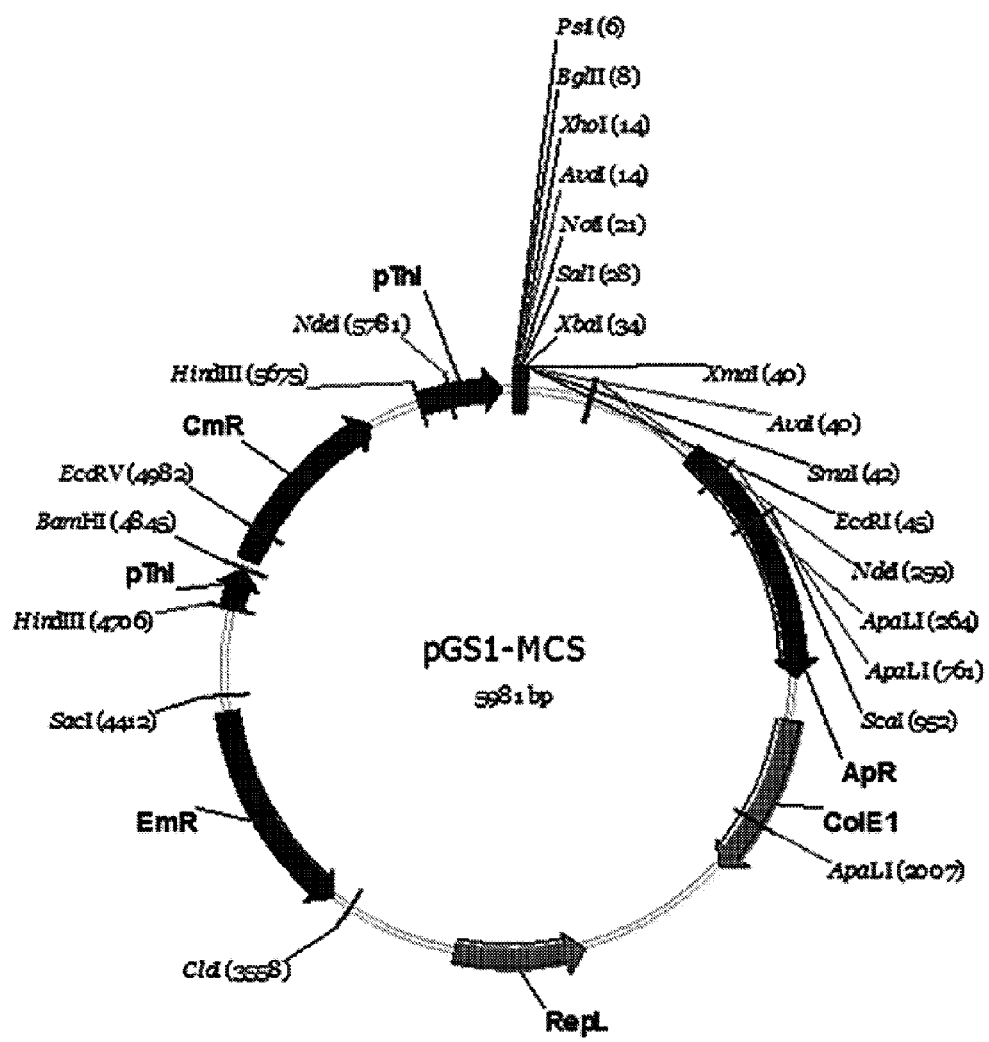
FIG. 3 shows a pGS1-MCS vector.
Figure 4:
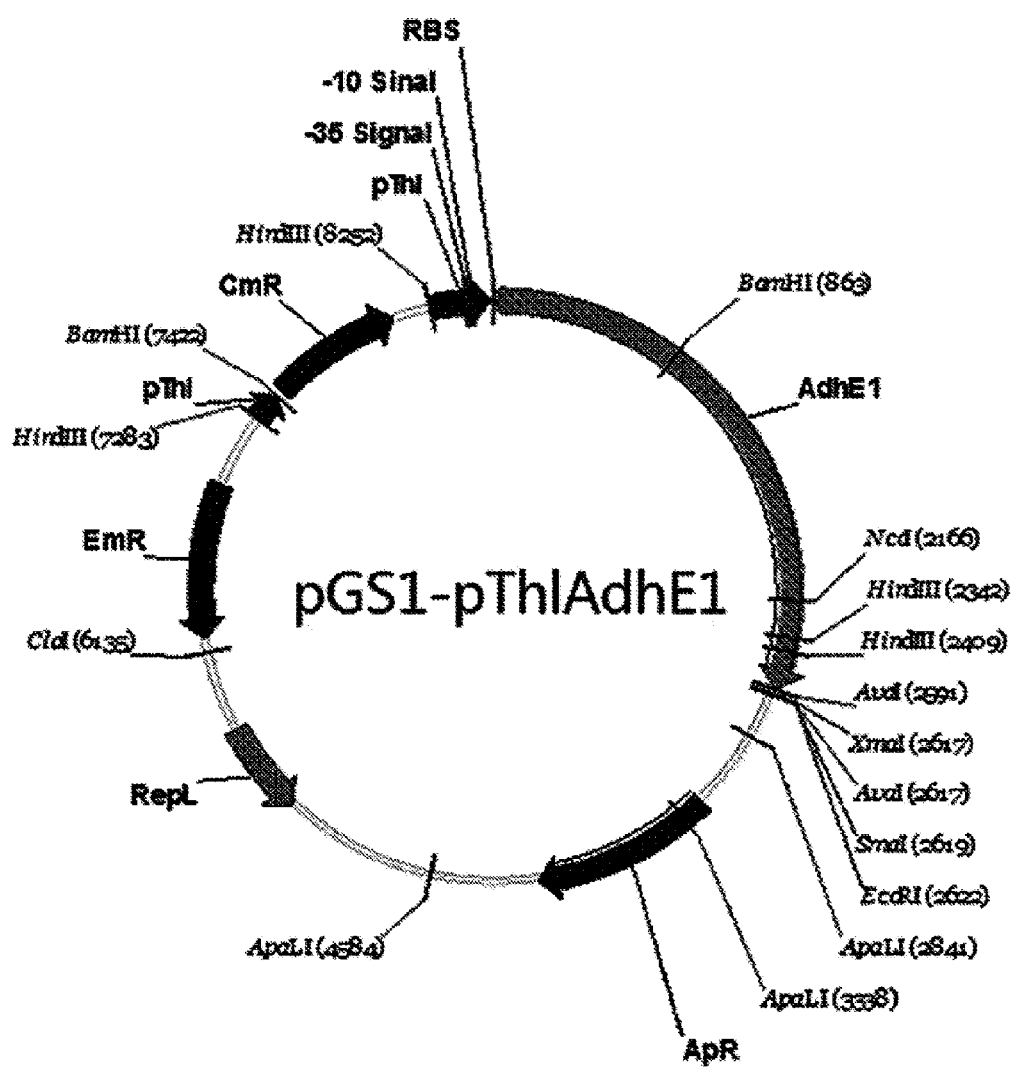
FIG. 4 shows pGS1-pTh1AdhE1.

The amplified gene was purified on a 1% agarose gel, and digested with PstI and XhoI restriction enzymes to carry out DNA fragmentation. Further, the resulting fragments were ligated into a pGS1-MCS vector (FIG. 3) digested with the same restriction enzymes to construct pGS1-pTh1AdhE1 (FIG. 4).

Figure 5:
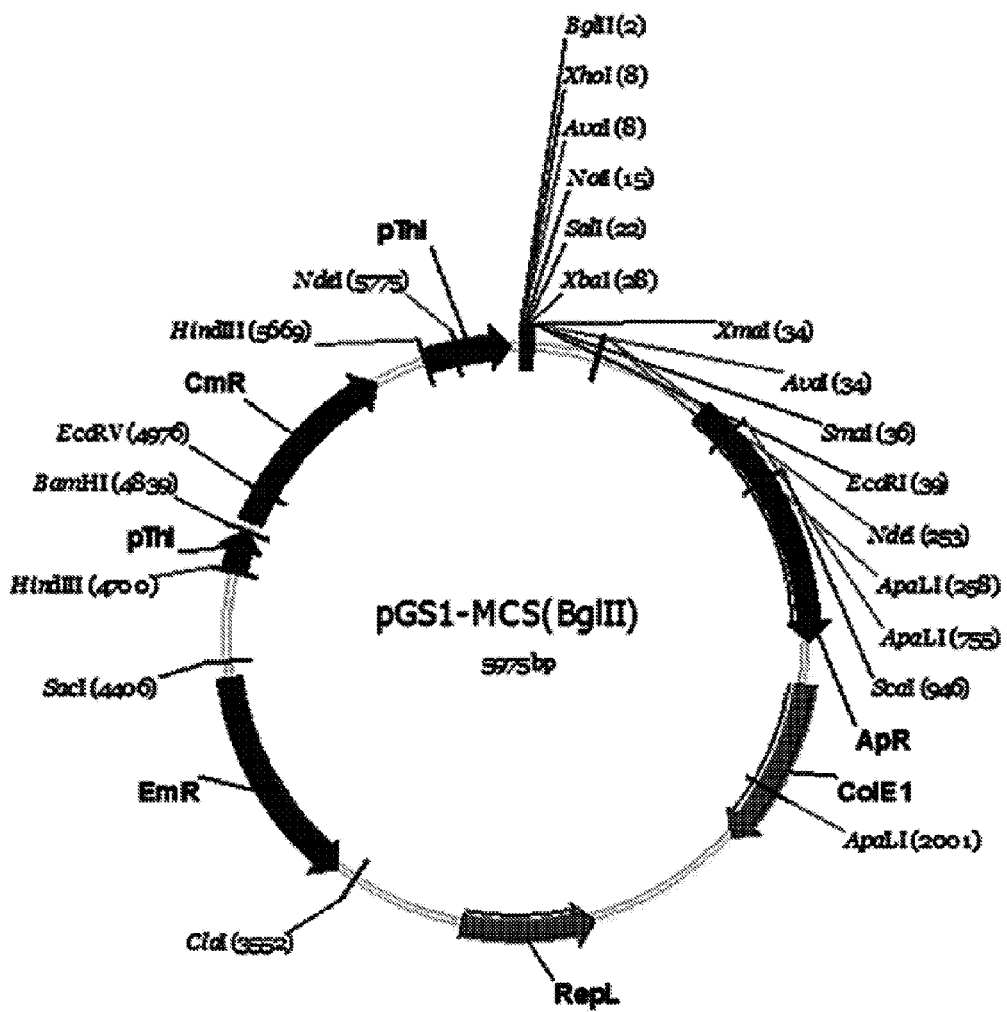
FIG. 5 shows a pGS1-MCS1(BglII) vector.
Figure 6:
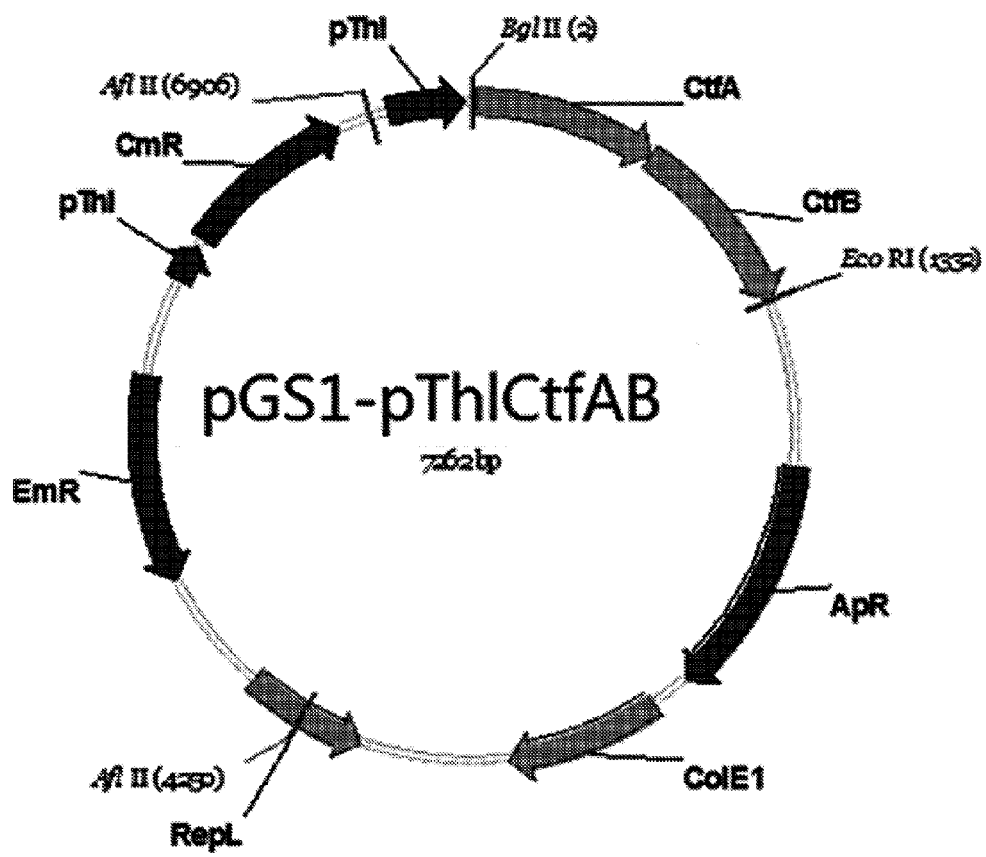
FIG. 6 shows pGS1-pTh1ctfAB.

Under the same conditions as mentioned above, ctfAB (SEQ ID NO: 2) of *Clostridium acetobutylicum* strain ATCC 824 was amplified using ctfAB-UP-Bgl II (SEQ ID NO: 5) primer and ctfAB-DN-EcoRI primer (SEQ ID NO: 6). The amplified gene was purified on a 1% agarose gel, and digested with BglII and EcoRI restriction enzymes to perform DNA fragmentation. Further, the resulting fragments were ligated to a pGS1-MCS1(BglII) vector (FIG. 5) to construct pGS1-pTh1CtfAB (FIG. 6).

Construction of pGS1-pTh1AdhE1-CtfAB pGS1-pTh1AdhE1-ctfAB was constructed using the recombinant plasmids constructed as mentioned above. First, pGS1-pTh1CtfAB constructed using primers CtfAB-UP-XhoI (SEQ ID NO: 7) and E1AB-DN-SalI (SEQ ID NO: 8) was used as a template to amplify ctfAB gene (SEQ ID NO: 2). 100 nl of PCR reaction mixture was prepared by adding 250 μM of dNTP, 20 pmol of each primer, 1.5 mM of MgCl$_2$, 10 μl of 10× buffer, 100 ng of DNA template, and 5 units of pfu polymerase. The reaction mixture was subjected to initial denaturation at 95° C. for 5 minutes, denaturation at 95° C. for 1 minute, annealing at 50° C. for 1 minute, and polymerization at 72° C. for 2 minutes. These processes were repeated 25 times.

Figure 7:
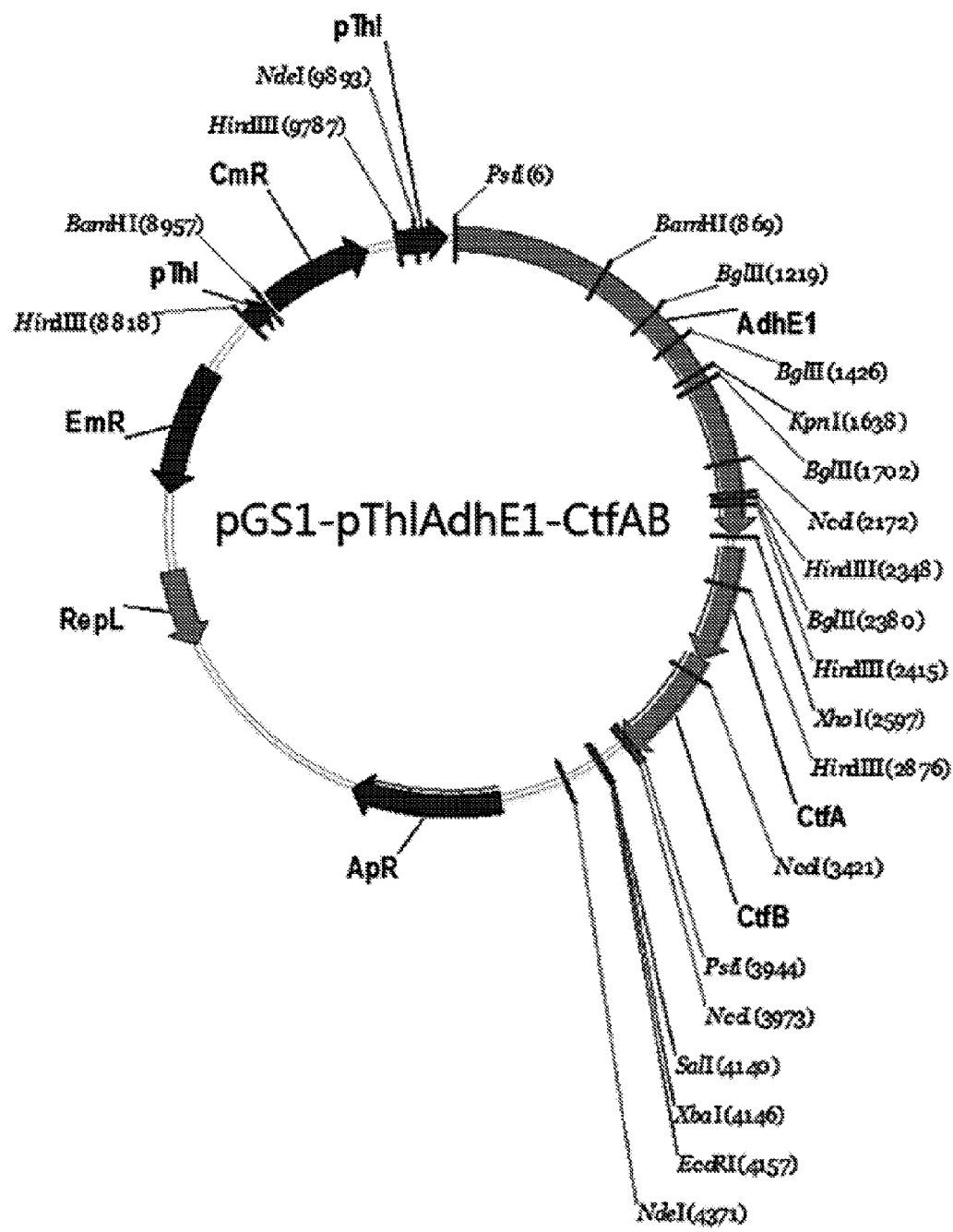
FIG. 7 shows pGS1-pTh1AdhE1-CtfAB.

The amplified gene was purified on a 1% agarose gel, and digested with XhoI and SalI restriction enzymes to carry out DNA fragmentation. Further, the resulting fragments were ligated to a pGS1-pTh1AdhE1 vector digested with the same restriction enzymes to construct pGS1-pTh1AdhE1-CtfAB (FIG. 7). The SEQ ID NOs: 1 and 2 are represented in FIGS. 8 and 9, respectively. SEQ ID NOs: 3 to 8 are as shown in Table 1. In addition, the characteristics of the recombinant plasmids are shown in Table 2.

TABLE 1

| | |
|---|---|
| SEQ ID NO: 3 | AdhE1-UP-PstI:<br>5'-CACCTGCAGATGAAAGTCACAACAGTA<br>AAGGAATTAGAT-3' |
| SEQ ID NO: 4 | AdhE1-DN-XhoI:<br>5'-CACCTCGAGTTAAGGTTGTTTTTTAAA<br>ACAATTTATATACA-3' |
| SEQ ID NO: 5 | CtfAB-UP-BglII:<br>5'-CACAGATCTATGAACTCTAAAATAATT<br>AGATTTGAAAATTTAAG-3' |
| SEQ ID NO: 6 | CtfAB-DN-EcoRI:<br>5'-CACGAATTCTTAAACAGCCATGGGTCT<br>AAGTTCATTGGATATGA-3 |
| SEQ ID NO: 7 | CtfAB-UP-XhoI:<br>5'-CACCTCGAGACCTTCATATTTCAACTA<br>CTTTTTAT-3' |
| SEQ ID NO: 8 | E1AB-DN-SalI:<br>5'-TACGCGTCGACGCCAGTAAAAGAGATT<br>GTTTCTAGC-3" |

TABLE 2

| Plasmid | Relative Characteristic |
|---|---|
| pGS1-MCS | Erm, cm |
| pGS1-MCS1(BglII) | Erm, cm |
| pGS1-pThlAdhE1 | Erm, cm |
| pGS1-pThlCtfAB | Erm, cm |
| pGS1-pThlAdhE1-CtfAB | Erm, cm |

Experimental Example 2

Preparation of Recombinant Microorganisms

Recombination plasmids constructed in Experimental Example 1 were introduced to organic acid-producing gene deleted strains in Table 3 to prepare transformed recombinant microorganisms.

TABEL 3

| Organic acid-producing gene deleted strain |
|---|
| Clostridium acetobutylicum ATCC824 Δpta |
| Clostridium acetobutylicum ATCC824 Δbuk |
| Clostridium acetobutylicum ATCC824 Δpta Δbuk |
| Clostridium acetobutylicum ATCC824 Δpta Δbuk Δadc |

Each organic acid-producing gene deleted Clostridium strain was cultured in 60 ml CGM liquid media (0.75 g/L $K_2HPO_4$, 0.75 g/L $KH_2PO_4$, 0.7 g/L, $MgSO_4 \cdot 7H_2O$, 0.017 g/L $MnSO_4 \cdot 5H_2O$, 0.01 g/L, $FeSO_4 \cdot 7H_2O$, 2 g/L $(NH_4)_2SO_4$, 1 g/L NaCl, 2 g/L asparagine, 0.004 g/L p-aminobenzoic acid, 5 g/L, yeast extract, 4.08 g/L $CH_3COONa \cdot 3H_2O$, and 80 g/L glucose) under anaerobic conditions until the absorbance at $600_{nm}$ (OD600) reached 0.5. The cultured broth was left on ice for 10 minutes, and then subjected to centrifugation at 7000 g for 10 minutes at 4° C. The cell pellets were washed with an electroporation buffer solution three times, followed by suspending in 2 ml of the same buffer solution to prepare cells for transformation. To 500 μl of the prepared cells for transformation, 0.5 μg to 2.0 μg of plasmids were added, followed by electroporation (4 mm cuvette, 2.5 kV, ∞Ω, 25 μF) using a Gene Pulser II (Bio-Rad Co., Ltd.). The resulting mixture was cultured anaerobically in a medium to which antibiotics were added to prepare transformed strains (Table 4).

All the plasmids used in transformation were prepared such that the plasmids were methylated in Escherichia coli strain TOP10 transformed with a pAN1 vector prior to the electroporation so as not to be affected by a restriction system of Clostridium strains.

TABLE 4

| # | Strain | Introduced plasmid |
|---|---|---|
| C1 | Clostridium acetobutylicum ATCC824 | — |
| 1 | Clostridium acetobutylicum ATCC824 Δpta | pGS1-pThlAdhE1 |
| 2 | Clostridium acetobutylicum ATCC824 Δbuk | pGS1-pThlAdhE1 |
| 3 | Clostridium acetobutylicum ATCC824 Δpta Δbuk | pGS1-pThlAdhE1 |
| 4 | Clostridium acetobutylicum ATCC824 Δpta | pGS1-pThlCtfAB |
| 5 | Clostridium acetobutylicum ATCC824 Δbuk | pGS1-pThlCtfAB |
| 6 | Clostridium acetobutylicum ATCC824 Δpta Δbuk | pGS1-pThlCtfAB |
| 7 | Clostridium acetobutylicum ATCC824 Δpta | pGS1-pThlAdhE1-CtfAB |
| 8 | Clostridium acetobutylicum ATCC824 Δbuk | pGS1-pThlAdhE1-CtfAB |

TABLE 4-continued

| # | Strain | Introduced plasmid |
|---|---|---|
| 9 | Clostridium acetobutylicum ATCC824 Δpta Δbuk | pGS1-pThlAdhE1-CtfAB |
| 10 | Clostridium acetobutylicum ATCC824 Δpta Δbuk Δadc | pGS1-pThlAdhE1-CtfAB |

Experimental Example 3

Production of Bio-Butanol by Batch Culture

Butanol production ability was tested through batch culture depending on recombinant microorganisms. The recombinant Clostridium strains prepared in Experimental Example 2 (#1 to #10) were plated onto CGM/Erythromycin or CGM/Chlorampenicol plates and anaerobically cultured overnight at 37° C. 50 ml disposable tubes (Falcon, USA) containing 40 ml of CCM/antibiotics were inoculated using each cultured colony, followed by standing at 37° C., and then anaerobically cultured until the absorbance at $600_{nm}$ (OD600) reached 1. CGM liquid media containing 400 ml of 6% glucose was inoculated with cultured seed microorganisms, followed by standing at 37° C., and then anaerobically cultured until the absorbance at $600_{nm}$ (OD600) reached 1~2. A fermenter containing 1.6 L of CGM liquid media containing 8% glucose was inoculated with the resulting seed microorganisms to perform cultivation. pH was adjusted to 5.0 during anaerobic culture using ammonium hydroxide (NH4OH). Anaerobic conditions were maintained while introducing nitrogen at a rate of 20 ml/min. The concentration of butanol and a mixed solvent was analyzed every three hours after cultivation.

As controls, wild type Clostridium acetobutylicum strain ATCC824 (C1), Clostridium acetobutylicum ATCC824 strains where organic acid producing genes were deleted (C2 to C4), and a Clostridium acetobutylicum ATCC824 Δpta Δbuk strain (C5) to which an expression vector was introduced were used (see C1 to C5 strains of Table 6).

Analysis of butanol and a mixed solvent was performed by gas chromatography (Agilent, USA) wherein the analysis conditions are as shown in Table 5. In addition, the concentration of sugars and organic acids was identified by centrifuging the cultured broth to yield a supernatant fluid, which was then analyzed by HPLC and a sugar analyzer. HPLC conditions were as follows: Water containing 0.01N sulfuric acid was used as a mobile phase; flow rate was 0.6 ml/min; and Aminex87H and Aminex87P (Bio-Rad, USA) were used as columns. The produced sugars and organic acids were analyzed using an RI (Reflective Index) detector.

TABLE 5

| | |
|---|---|
| Injector temperature | 320° C. |
| Detector temperature | 320° C. |
| Injector Split ratio | 20/1 |
| Injection volume | 0.1 ul |
| Oven condition | 80° C./15 min |
| Air flow | 300 mL/min |
| H2 flow | 30 mL/min |
| Column | Supelco CarboWAX |

As a result, in the case of pta deleted strain (C2), it was found that productivity and yield were increased 2.3 times, 2% or more, respectively, as compared to the wild type strain (C1). In addition, in the case of buk deleted strain (C3), it was found that productivity and yield were increased 1.5 times, and 6% or more, respectively, as compared to the wild type strain (C1). Specifically, in the case of pta and buk deleted strain (C4), butanol selectivity, productivity and yield were increased 8.9%, 1.5 times, and 4%, respectively. In view of the above results, it was determined that deletions of the organic acid producing genes increased yield, butanol production and selectivity the most.

In the case where AdhE1 was overexpressed in a pta deleted strain (#1), it was found that yield was increased 7%. In the case where AdhE1 was overexpressed in a pta and buk deleted strain (#3), it was found that butanol productivity and yield were increased by 1.7 times and 6%, respectively.

Further, in the case where ctfAB was overexpressed in a pta deleted strain (#4), yield was increased by 3% owing to the overexpression. In the case where ctfAB was overexpressed in buk deleted strain (#5), it was found that productivity and yield were increased 1.13 times and 2%, respectively, owing to the overexpression. In addition, in the case where ctfAB was overexpressed in a pta and buk deleted strain (#6), it was found that productivity and yield were increased 1.6 times and 4%, respectively, owing to overexpression.

Specifically, in the case where pta and buk were deleted simultaneously and AdhE1 and CtfAB were overexpressed simultaneously (#9), it was found that yield, butanol productivity and butanol selectivity were the highest.

On the other hand, in order to further increase yield, butanol productivity and butanol selectivity in general by inhibiting the production of acetone, strain #10 was constructed by deleting adc, namely, a gene encoding an acetoacetate decarboxylase which synthesizes acetone in strain #9. However, it was found that, as intended, acetone production was decreased and butanol selectivity was increased, while butanol production amount was decreased, and yield and butanol productivity were greatly decreased 6%, and 0.5 times, respectively, as compared to strain #9. It was determined that this was because acetoacetate was not capable of being converted to acetone, thereby causing cytotoxicity (Table 6).

Experimental Example 4

Production of Bio-Butanol by Continuous Culture

Strain #9, which was determined to have good butanol selectivity, butanol productivity and yield in Experimental Example 3 was evaluated as to performance and stability through continuous culture.

First, a fermentor for continuous fermentation was manufactured. In order to prevent loss of an adsorbent due to elution, two 3 L columns were provided at upper and lower portions thereof with about 150 nm filters, provided with a stirrer, and then filled with 200 g of an adsorbent to complete two columns a and b. These columns were connected to the fermentor using a silicon tube, to which a pump was disposed such that a culture broth could be circulated. An inlet and an outlet of each of the columns were provided with a 4-way valve such that the adsorbent in the columns could be desorbed in real time by flowing a solvent for elution when the adsorbent was saturated with butanol and a mixed solvent, in which the culture broth was continuously circulated to a second column. Although the culture broth was circulated from top to bottom, the circulation direction does not matter.

Strain #9 having butanol and mixed solvent (ABE) production ability was cultured using the incubator manufactured above. First, to a reactor having 3.2 L of CGM liquid media, 800 ml of seed microorganism anaerobically cultured overnight in CGM liquid media was inoculated to perform cultivation. The seed microorganism was cultured by general batch fermentation. When butanol concentration reached about 7 g/L~8 g/L, the culture broth was passed through a column at a rate of 50 ml/min via a pump to circulate the culture. As the culture broth was passed through the column, the adsorbent was suspended in the culture broth to form a diluted slurry, thereby allowing the culture broth to pass through the column without plugging due to cell flock. The butanol concentration was maintained at 8 g/L or less by evaluating samples taken before and after passing through the column. The concentration of butanol and a mixed solvent was analyzed through gas chromatography. The sugar concentration during the culture procedure was maintained at 20 g/L using HPLC and a sugar analyzer.

As a result, 53 hours of continuous cultivation was stably performed. It was found that the strain demonstrated enhanced butanol productivity and yield (Table 7).

TABLE 6

| # | Strain | Introduced plasmid | acetone (g/L) | ethanol (g/L) | Butanol (g/L) | Total ABE (g/L) | Butanol Selectivity (%) | Butanol Productivity (g/L/h)* | Yield (%) |
|---|---|---|---|---|---|---|---|---|---|
| C1 | C. acetobutylicum ATCC824 | — | 4.413 | 0.981 | 12.784 | 18.18 | 70.3 | 0.489 | 22 |
| C2 | C. acetobutylicum ATCC824 Δpta | — | 3.521 | 1.519 | 12.160 | 17.20 | 70.7 | 1.114 | 24 |
| C3 | C. acetobutylicum ATCC824 Δbuk | — | 5.176 | 1.328 | 13.768 | 20.27 | 67.9 | 0.726 | 28 |
| C4 | C. acetobutylicum ATCC824 Δpta Δbuk | — | 2.764 | 0.979 | 14.262 | 18.01 | 79.2 | 0.721 | 28 |
| C5 | C. acetobutylicum ATCC824 Δpta Δbuk | pGS1-MCS | 2.100 | 0.944 | 13.466 | 16.51 | 81.6 | 0.770 | 28 |
| 1 | C. acetobutylicum ATCC824 Δpta | pGS1-pThlAdhE1 | 4.034 | 2.437 | 14.547 | 21.02 | 69.2 | 0.970 | 31 |
| 2 | C. acetobutylicum ATCC824 Δbuk | pGS1-pThlAdhE1 | 2.842 | 4.362 | 13.347 | 20.55 | 64.9 | 0.792 | 29 |
| 3 | C. acetobutylicum ATCC824 Δpta Δbuk | pGS1-pThlAdhE1 | 1.804 | 3.151 | 17.165 | 22.12 | 77.6 | 1.239 | 34 |
| 4 | C. acetobutylicum ATCC824 Δpta | pGS1-pThlCtfAB | 5.935 | 1.184 | 14.398 | 21.52 | 66.9 | 1.135 | 27 |
| 5 | C. acetobutylicum ATCC824 Δbuk | pGS1-pThlCtfAB | 5.941 | 1.421 | 13.043 | 20.41 | 63.9 | 0.821 | 30 |
| 6 | C. acetobutylicum ATCC824 Δpta Δbuk | pGS1-pThlCtfAB | 2.462 | 1.674 | 16.628 | 20.76 | 80.1 | 1.155 | 32 |
| 7 | C. acetobutylicum ATCC824 Δpta | pGS1-pThlAdhE1-ctfAB | 5.452 | 1.951 | 16.317 | 23.72 | 68.3 | 1.341 | 30 |
| 8 | C. acetobutylicum ATCC824 Δbuk | pGS1-pThlAdhE1-ctfAB | 2.851 | 4.497 | 13.318 | 20.67 | 64.4 | 1.001 | 30 |
| 9 | C. acetobutylicum ATCC824 Δpta Δbuk | pGS1-pThlAdhE1-ctfAB | 1.315 | 2.386 | 14.813 | 18.513 | 80.0 | 1.310 | 32 |
| 10 | C. acetobutylicum ATCC824 Δpta Δbuk Δadc | pGS1-pThlAdhE1-CtfAB | 0.204 | 1.104 | 11.715 | 13.02 | 90.0 | 0.818 | 27 |

TABLE 7

| | ABE production amount (g) | | | Total ABE production amount | Yield (%) | ABE Productivity (g/L/h) | Butanol Selectivity (%) | Cultivation Time (h) | Glucose consumed amount (g) |
|---|---|---|---|---|---|---|---|---|---|
| # | Acetone | Ethanol | Butanol | | | | | | |
| 9 | 19.075 | 141.530 | 404.856 | 565.459 | 36.6 | 2.67 | 77.2 | 53 | 1546.870 |

INDUSTRIAL APPLICABILITY

The present invention relates to a recombinant microorganism having an increased ability to produce butanol, wherein the microorganism has an acetyl-CoA biosynthetic pathway and a butyryl-CoA biosynthetic pathway, and wherein a pathway of converting acetyl-CoA to acetate is suppressed and a pathway of converting acetate to acetyl-CoA and a pathway of converting butyryl-CoA to butanol are promoted. In addition, the present invention relates to a method for producing butanol using the recombinant microorganism.

The invention claimed is:

1. A recombinant *Clostridium acetobutylicum* microorganism having enhanced butanol producing ability in comparison to a wild type *Clostridium acetobutylicum* microorganism,
   wherein the recombinant *Clostridium acetobutylicum* microorganism has inactivated or deleted chromosomal phosphotransacetylase (pta) and butyrate kinase (buk) genes,
   wherein the recombinant *Clostridium acetobutylicum* microorganism has increased expression of a CoA transferase (ctfAB) gene and an alcohol/aldehyde dehydrogenase (adhE) gene in comparison to the wild type *Clostridium acetobutylicum* microorganism, and
   wherein the recombinant *Clostridium acetobutylicum* microorganism has an acetyl-CoA biosynthetic pathway and a butyryl-CoA biosynthetic pathway.

2. The recombinant microorganism according to claim 1, wherein a gene encoding acetoacetate decarboxylase is not deleted.

3. The recombinant microorganism according to claim 1, wherein butanol selectivity is 60% or more based on batch culture.

4. The recombinant microorganism according to claim 1, wherein butanol productivity is 1.3 g/L/h or more based on batch culture.

5. The recombinant microorganism according to claim 1, wherein butanol yield is 28% or more based on batch culture.

6. A method for producing butanol comprising:
   culturing the recombinant microorganism according to claim 1 in a culture solution to produce butanol; and
   harvesting the butanol from the culture solution.

7. A method for producing butanol comprising:
   culturing the recombinant microorganism according to claim 2 in a culture solution to produce butanol; and
   harvesting the butanol from the culture solution.

8. A method for producing butanol comprising:
   culturing the recombinant microorganism according to claim 3 in a culture solution to produce butanol; and
   harvesting the butanol from the culture solution.

9. A method for producing butanol comprising:
   culturing the recombinant microorganism according to claim 4 in a culture solution to produce butanol; and
   harvesting the butanol from the culture solution.

10. A method for producing butanol comprising:
    culturing the recombinant microorganism according to claim 5 in a culture solution to produce butanol; and
    harvesting the butanol from the culture solution.

* * * * *